United States Patent
Anderson

(10) Patent No.: US 9,302,084 B2
(45) Date of Patent: Apr. 5, 2016

(54) SUBINTIMAL RECANALIZATION WITH BIO-ABSORBABLE STENT

(71) Applicant: Boston Scientific Scimed, Inc., Maple Grove, MN (US)

(72) Inventor: James Anderson, Fridley, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 309 days.

(21) Appl. No.: 13/707,734

(22) Filed: Dec. 7, 2012

(65) Prior Publication Data

US 2013/0150880 A1 Jun. 13, 2013

Related U.S. Application Data

(60) Provisional application No. 61/568,903, filed on Dec. 9, 2011.

(51) Int. Cl.

| | |
|---|---|
| A61F 2/958 | (2013.01) |
| A61M 29/02 | (2006.01) |
| A61B 17/3207 | (2006.01) |
| A61M 25/10 | (2013.01) |
| A61B 17/22 | (2006.01) |
| A61F 2/00 | (2006.01) |
| A61M 25/01 | (2006.01) |

(52) U.S. Cl.
CPC ............ *A61M 29/02* (2013.01); *A61B 17/3207* (2013.01); *A61F 2/958* (2013.01); *A61B 2017/22095* (2013.01); *A61F 2002/0086* (2013.01); *A61F 2002/9583* (2013.01); *A61F 2210/0004* (2013.01); *A61M 25/1002* (2013.01); *A61M 2025/0197* (2013.01)

(58) Field of Classification Search
CPC ................. A61M 25/1002; A61M 2025/0197; A61M 2025/1045; A61M 29/02; A61F 2/958; A61F 2002/9583; A61F 2/954; A61F 2002/0086; A61F 2002/821; A61F 2210/0004; A61B 2017/22095; A61B 17/3207
USPC ................. 606/194, 198; 623/1.11, 1.12, 1.14
See application file for complete search history.

(56) References Cited

U.S. PATENT DOCUMENTS

| | | | | |
|---|---|---|---|---|
| 5,049,131 A | * | 9/1991 | Deuss | ......................... 604/98.01 |
| 5,458,639 A | | 10/1995 | Tsukashima et al. | |
| 5,749,890 A | * | 5/1998 | Shaknovich | ................... 606/198 |
| 5,792,106 A | * | 8/1998 | Mische | ..................... 604/103.01 |

(Continued)

FOREIGN PATENT DOCUMENTS

| | | |
|---|---|---|
| EP | 1430925 A1 | 6/2004 |
| EP | 2133114 A1 | 12/2009 |

*Primary Examiner* — Ryan J Severson
*Assistant Examiner* — Christian Knauss
(74) *Attorney, Agent, or Firm* — Seager, Tufte & Wickhem LLP

(57) ABSTRACT

A recanalization catheter assembly and method for establishing a subintimal pathway around an occlusion in a blood vessel. The recanalization catheter assembly an inflatable balloon structure including a distal anchoring portion configured to expand within a true lumen portion of the blood vessel distal of the occlusion to anchor the recanalization catheter from unintentional movement during expansion of a stent in the subintimal pathway. The expandable stent, such as a bio-absorbable stent, may be configured to promote native tissue regrowth around the stent to create a superficial intimal layer along the subintimal pathway.

11 Claims, 9 Drawing Sheets

(56) References Cited

U.S. PATENT DOCUMENTS

| | | | |
|---|---|---|---|
| 5,830,222 A | 11/1998 | Makower et al. | |
| 5,935,108 A | 8/1999 | Katoh et al. | |
| 5,935,135 A * | 8/1999 | Bramfitt et al. | 623/1.11 |
| 5,938,671 A | 8/1999 | Katoh et al. | |
| 5,968,064 A | 10/1999 | Selmon et al. | |
| 6,010,449 A | 1/2000 | Selmon et al. | |
| 6,027,510 A * | 2/2000 | Alt | 606/108 |
| 6,068,638 A | 5/2000 | Makower et al. | |
| 6,120,516 A | 9/2000 | Selmon et al. | |
| 6,159,219 A * | 12/2000 | Ren | 606/108 |
| 6,159,225 A | 12/2000 | Makower et al. | |
| 6,190,353 B1 | 2/2001 | Makower et al. | |
| 6,196,230 B1 * | 3/2001 | Hall et al. | 128/898 |
| 6,200,325 B1 * | 3/2001 | Durcan et al. | 606/108 |
| 6,217,527 B1 | 4/2001 | Selmon et al. | |
| 6,217,549 B1 | 4/2001 | Selmon et al. | |
| 6,221,049 B1 | 4/2001 | Selmon et al. | |
| 6,231,546 B1 | 5/2001 | Milo et al. | |
| 6,231,587 B1 * | 5/2001 | Makower | 606/198 |
| 6,235,000 B1 | 5/2001 | Milo et al. | |
| 6,241,667 B1 | 6/2001 | Vetter et al. | |
| 6,364,900 B1 * | 4/2002 | Heuser | 623/1.11 |
| 6,398,798 B2 | 6/2002 | Selmon et al. | |
| 6,500,147 B2 | 12/2002 | Omaleki et al. | |
| 6,506,178 B1 | 1/2003 | Schubart et al. | |
| 6,508,825 B1 | 1/2003 | Selmon et al. | |
| 6,511,458 B2 | 1/2003 | Milo et al. | |
| 6,514,217 B1 | 2/2003 | Selmon et al. | |
| 6,551,314 B1 | 4/2003 | Hill et al. | |
| 6,554,795 B2 | 4/2003 | Bagaoisan et al. | |
| 6,579,302 B2 | 6/2003 | Duerig et al. | |
| 6,599,304 B1 | 7/2003 | Selmon et al. | |
| 6,638,247 B1 | 10/2003 | Selmon et al. | |
| 6,663,577 B2 * | 12/2003 | Jen et al. | 600/585 |
| 6,682,542 B2 | 1/2004 | Harkrider | |
| 6,719,725 B2 | 4/2004 | Milo et al. | |
| 6,719,934 B2 | 4/2004 | Stinson | |
| 6,736,827 B1 | 5/2004 | McAndrew et al. | |
| 6,955,175 B2 | 10/2005 | Stevens et al. | |
| 7,004,173 B2 | 2/2006 | Sparks et al. | |
| 7,083,639 B2 * | 8/2006 | Guinan et al. | 623/1.1 |
| 7,169,160 B1 | 1/2007 | Middleman et al. | |
| 7,179,270 B2 * | 2/2007 | Makower | 606/159 |
| 7,179,280 B2 | 2/2007 | Mills | |
| 7,226,472 B2 * | 6/2007 | Pederson et al. | 623/1.11 |
| 7,229,421 B2 | 6/2007 | Jen et al. | |
| 7,357,794 B2 | 4/2008 | Makower et al. | |
| 7,594,928 B2 | 9/2009 | Headley, Jr. et al. | |
| 7,637,940 B2 | 12/2009 | Kocur et al. | |
| 7,699,887 B2 | 4/2010 | Burnside et al. | |
| 7,740,623 B2 | 6/2010 | Nayak et al. | |
| 7,938,819 B2 | 5/2011 | Kugler et al. | |
| 7,998,162 B2 * | 8/2011 | Ho et al. | 606/194 |
| 2001/0000041 A1 * | 3/2001 | Selmon et al. | 600/585 |
| 2001/0012924 A1 | 8/2001 | Milo et al. | |
| 2001/0034547 A1 * | 10/2001 | Hall et al. | 623/1.11 |
| 2002/0103459 A1 | 8/2002 | Sparks et al. | |
| 2002/0120320 A1 * | 8/2002 | Wang et al. | 623/1.11 |
| 2002/0120321 A1 * | 8/2002 | Gunderson et al. | 623/1.11 |
| 2002/0128677 A1 | 9/2002 | Duerig et al. | |
| 2003/0120195 A1 | 6/2003 | Milo et al. | |
| 2003/0139763 A1 | 7/2003 | Duerig et al. | |
| 2003/0236542 A1 * | 12/2003 | Makower | 606/167 |
| 2004/0167554 A1 | 8/2004 | Simpson et al. | |
| 2004/0186507 A1 | 9/2004 | Hall et al. | |
| 2004/0230219 A1 | 11/2004 | Roucher, Jr. | |
| 2005/0171478 A1 | 8/2005 | Selmon et al. | |
| 2005/0267561 A1 * | 12/2005 | Jones et al. | 623/1.11 |
| 2006/0009832 A1 * | 1/2006 | Fisher | 623/1.11 |
| 2006/0094930 A1 | 5/2006 | Sparks et al. | |
| 2006/0135985 A1 * | 6/2006 | Cox et al. | 606/194 |
| 2006/0184011 A1 | 8/2006 | MacAulay et al. | |
| 2006/0271151 A1 * | 11/2006 | McGarry et al. | 623/1.11 |
| 2006/0276749 A1 | 12/2006 | Selmon et al. | |
| 2007/0038283 A1 * | 2/2007 | Mustapha | 623/1.11 |
| 2007/0093779 A1 | 4/2007 | Kugler et al. | |
| 2007/0093780 A1 * | 4/2007 | Kugler et al. | 604/510 |
| 2007/0093781 A1 * | 4/2007 | Kugler et al. | 604/510 |
| 2007/0093782 A1 | 4/2007 | Kugler et al. | |
| 2007/0219576 A1 * | 9/2007 | Cangialosi | 606/198 |
| 2007/0265596 A1 | 11/2007 | Jen et al. | |
| 2008/0033423 A1 | 2/2008 | Peacock | |
| 2008/0125748 A1 * | 5/2008 | Patel | 604/509 |
| 2008/0143067 A1 | 6/2008 | Wicka | |
| 2008/0154172 A1 | 6/2008 | Mauch | |
| 2008/0200896 A1 | 8/2008 | Shmulewitz et al. | |
| 2008/0228171 A1 * | 9/2008 | Kugler et al. | 604/529 |
| 2008/0243065 A1 | 10/2008 | Rottenberg et al. | |
| 2008/0243168 A1 * | 10/2008 | Ho et al. | 606/194 |
| 2008/0249397 A1 | 10/2008 | Kapadia | |
| 2009/0005755 A1 | 1/2009 | Keith et al. | |
| 2009/0088685 A1 | 4/2009 | Kugler et al. | |
| 2009/0093791 A1 | 4/2009 | Heuser | |
| 2009/0124899 A1 * | 5/2009 | Jacobs et al. | 600/434 |
| 2009/0182412 A1 * | 7/2009 | Tan | A61F 2/95 623/1.12 |
| 2009/0209910 A1 * | 8/2009 | Kugler et al. | 604/103.1 |
| 2009/0228171 A1 | 9/2009 | Goff et al. | |
| 2009/0254113 A1 * | 10/2009 | Nolan et al. | 606/194 |
| 2009/0264826 A1 * | 10/2009 | Thompson | 604/164.13 |
| 2009/0292296 A1 | 11/2009 | Pansky et al. | |
| 2009/0299171 A1 | 12/2009 | Duffy et al. | |
| 2009/0299402 A1 | 12/2009 | Orihashi et al. | |
| 2010/0063534 A1 | 3/2010 | Kugler et al. | |
| 2010/0069945 A1 | 3/2010 | Olson et al. | |
| 2010/0125244 A1 | 5/2010 | McAndrew | |
| 2010/0317973 A1 * | 12/2010 | Nita | 600/467 |
| 2011/0112564 A1 | 5/2011 | Wolf | |
| 2011/0144677 A1 * | 6/2011 | Ward et al. | 606/170 |

\* cited by examiner

SUBINTIMAL RECANALIZATION WITH BIO-ABSORBABLE STENT

CROSS-REFERENCE TO RELATED APPLICATIONS

This application claims the benefit of U.S. Provisional Application No. 61/568,903, filed on Dec. 9, 2011, the entire disclosure of which is incorporated herein by reference.

TECHNICAL FIELD

The disclosure is directed to devices and methods for recanalization of an occluded blood vessel. More particularly, the disclosure is directed to devices and methods for positioning a stent in a created subintimal space of a blood vessel to form a pathway bypassing an occluded portion of the true lumen of the blood vessel.

BACKGROUND

Chronic total occlusion (CTO) is an arterial vessel blockage that obstructs blood flow through the vessel, and can occur in both coronary and peripheral arteries. In some instances, it may be difficult or impossible to pass through the CTO with a medical device in an antegrade direction to recanalize the vessel. Accordingly, techniques have been developed for creating a subintimal pathway (i.e., a pathway between the intimal and adventitial tissue layers of the vessel) around the occlusion and then re-entering the true lumen of the vessel distal of the occlusion in an attempt to recanalize the vessel. Accordingly, it is desirable to provide alternative recanalization devices and/or methods of recanalizing a blood vessel in which a CTO is present.

SUMMARY

The disclosure is directed to several alternative designs, materials and methods of manufacturing medical device structures and assemblies, and uses thereof.

Accordingly, one illustrative embodiment is a recanalization catheter assembly for establishing a subintimal pathway around an occlusion in a blood vessel. The recanalization catheter assembly includes an elongate catheter shaft extending distally from a hub assembly and an inflatable balloon structure mounted on a distal portion of the catheter shaft. The inflatable balloon structure is configured to be expanded from a deflated configuration to an inflated configuration with a fluid delivered to an interior of the inflatable balloon structure through an inflation lumen extending through the catheter shaft. A stent surrounds a body portion of the inflatable balloon structure, with a distal anchoring portion of the inflatable balloon structure positioned distal of the stent. The distal anchoring portion of the inflatable balloon structure is configured to expand within a true lumen portion of the blood vessel distal of the occlusion to anchor the recanalization catheter from unintentional movement during expansion of the stent in the subintimal pathway.

Another illustrative embodiment is a method of recanalizing a blood vessel by establishing a subintimal pathway around an occlusion. The method includes initially creating a subintimal pathway between a proximal opening into a vessel wall proximal of an occlusion and a distal opening into the vessel wall distal of the occlusion. An expandable stent is positioned in the subintimal pathway and then the expandable stent is expanded in the subintimal pathway. Thereafter, native tissue regrowth is promoted around the stent to create a superficial intimal layer along the subintimal pathway.

Yet another illustrative embodiment is a method of recanalizing a blood vessel by establishing a subintimal pathway around an occlusion. The method includes initially creating a subintimal pathway between a proximal opening into a vessel wall proximal of an occlusion and a distal opening into the vessel wall distal of the occlusion. An expandable stent surrounding a body portion of an inflatable balloon structure is positioned in the subintimal pathway with a distal anchoring portion of the inflatable balloon structure positioned in a true lumen portion of the blood vessel distal of the occlusion. The distal anchoring portion of the inflatable balloon structure is then inflated in the true lumen portion distal of the occlusion and the body portion of the inflatable balloon structure is inflated to expand the expandable stent in the subintimal pathway. The inflated distal anchoring portion anchors the inflatable balloon structure from unintentional proximal movement while the stent is expanded in the subintimal pathway to maintain proper placement of the stent in the subintimal pathway.

The above summary of some example embodiments is not intended to describe each disclosed embodiment or every implementation of the aspects of the disclosure.

BRIEF DESCRIPTION OF THE DRAWINGS

The aspects of the disclosure may be more completely understood in consideration of the following detailed description of various embodiments in connection with the accompanying drawings, in which.

Figure 1:
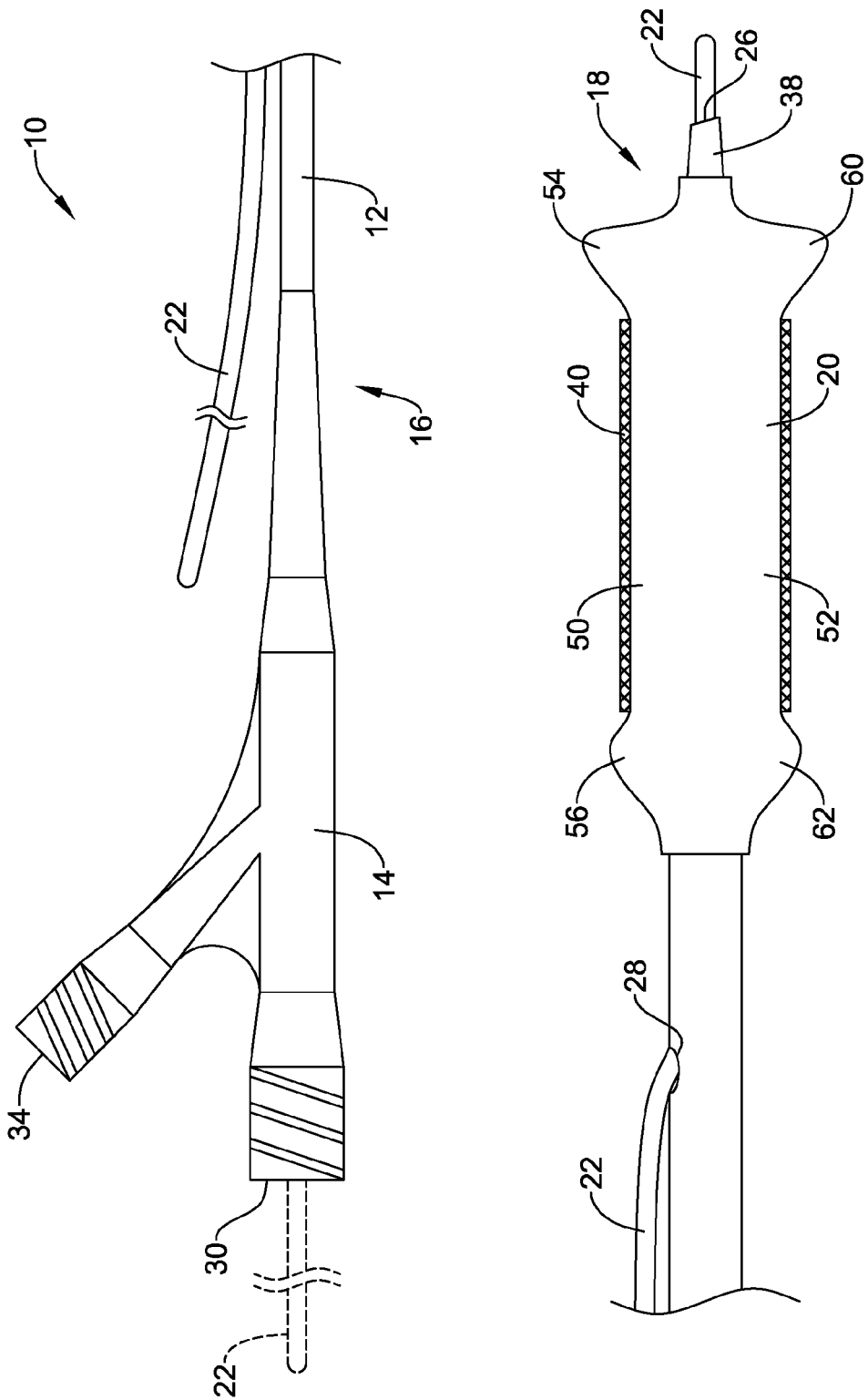
FIG. 1 is a side plan view of an exemplary catheter apparatus for recanalization of a blood vessel.

While the aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

An exemplary recanalization catheter 10 is illustrated at FIG. 1. The recanalization catheter 10, shown as a stent delivery catheter, may include a main catheter shaft 12 extending from a hub assembly 14 at a proximal end 16 of the catheter shaft 12 to an expandable member, shown as an inflatable balloon structure 20 mounted on a distal portion of the catheter shaft 12 proximate the distal end 18 of the catheter shaft 12. In some instances, the catheter shaft 12, or a proximal portion thereof proximal of the balloon structure 20 may include a slotted hypotube, such as a spiral slotted hypotube, to provide torsional rigidity and/or pushability of the catheter shaft 12 during use. A stent 40 may be positioned around a body portion 52 of the balloon structure 20 for delivery to a target location.

The catheter 10 may be configured to be advanced over a guidewire 22 for delivery to a remote location in the vasculature of a patient. For example, in some instances the catheter 10 may be configured as a single-operator-exchange (SOE) catheter having a guidewire lumen extending from a distal port 26 to a proximal guidewire port 28 located a short distance proximal of the balloon structure 20 and distal of the hub assembly 14. In such a configuration, the guidewire 22 may extend through the guidewire lumen between the distal port 26 and the proximal port 28, and extend along an exterior of the catheter shaft 12 proximal of the proximal port 28 to the proximal end 16 of the catheter shaft 12. In other instances, the catheter 10 may be configured as an over-the-wire (OTW) catheter having a guidewire lumen extending through the entire length of the catheter shaft 12 from a distal port 26 at a distal tip of the catheter 10 to a proximal guidewire port 30 in the hub assembly 14. FIG. 1 illustrates such a configuration with the proximally extending portion of the guidewire 22 in dashed lines. It is noted that in instances in which the catheter 10 is an SOE catheter, the hub assembly 14 may not include a proximal guidewire port 30 and/or in instances in which the catheter 10 is an OTW catheter, the proximal guidewire port 28 may not be present. In other instances, the catheter 10 may be configured as a fixed-wire catheter having a steerable wire portion forming the distalmost extent of the catheter 10.

The catheter shaft 12 may also include an inflation lumen extending from an inflation port 34 of the hub assembly 14 to an interior of the balloon structure 20. The inflation lumen may be configured for delivering inflation fluid to the balloon structure 20 to inflate the balloon structure 20, or portions thereof, during a medical procedure. In some instances, the catheter shaft 12 may include a plurality of inflation lumens in fluid communication with separate inflatable portions of the balloon structure 20 such that individual portions of the balloon structure 20 may be inflated independently.

In some embodiments, the catheter shaft 12, or a portion thereof, may include an outer tubular member and an inner tubular member extending through the outer tubular member and defining the guidewire lumen. The space between the inner tubular member and the outer tubular member may define the inflation lumen. In such embodiments, the main catheter shaft 12 may be configured such that the proximal waist of the balloon structure 20 is secured to the distal end of the outer tubular member, while the distal waist of the balloon structure 20 is secured to the distal end of the inner tubular member, extending through the interior of the balloon structure 20.

In other embodiments, the catheter shaft 12, or a portion thereof, may be an extruded shaft having a plurality of lumens formed therein. For example, the extruded shaft may include the guidewire lumen and the inflation lumen extending in a side-by-side arrangement. In such embodiments, the main catheter shaft 12 may be configured such that the proximal waist of the balloon structure 20 is secured to a portion of the extruded shaft, while the distal waist of the balloon structure 20 is secured to another portion of the extruded shaft or a tubular member extending therefrom, extending through the interior of the balloon structure 20.

The catheter 10 may also include a distal tip 38 extending distally from the balloon structure 20. The distal tip 38 may have a lumen extending therethrough and opening out to the distal port 26 at the distal end thereof to accommodate the guidewire 22 extending from the distal port 26. In some instances, the distal tip 38 may be an atraumatic tip, such as a flexible, low durometer tip similar to tips provided with typical angioplasty balloon catheters. However, in other embodiments, the distal tip 38 may be configured to facilitate piercing and/or dissection of tissue layers of the blood vessel. For example, the distal tip 38 may include a sharp, rigid and/or piercing feature. In one embodiment, as shown in FIG. 1, the distal tip 38 may include an angled distal edge, providing the distal tip 38 with a sharpened cutting or piercing edge.

As noted above, the recanalization catheter 10 may be a stent delivery catheter 10 configured to deliver a stent 40 to a subintimal pathway formed in a vessel wall to bypass an occlusion. As used herein, the term "stent" is intended to include stents, covered stents, stent-grafts, grafts and other expandable prosthetic devices for implantation in a body passageway to support the passageway. The stents may be self-expanding, expanded by an internal radial force (e.g., through inflation of a balloon), or a combination of self-expanding and balloon expandable.

The stent 40, or portions thereof, may be formed of a bioabsorbable material. Some exemplary bioabsorbable metallic materials include iron magnesium alloys. Some exemplary bioabsorbable polymeric materials include polylactide (PLA), poly-L-lactide (PLLA), poly-D-lactide (PDLA), polyglycolide (PGA), polycaprolactone, polydioxanone, and tyrosine polycarbonate. Some exemplary bioabsorbable stent configurations are disclosed in U.S. Pat. Nos. 7,699,887; 7,637,940; 7,594,928; 6,719,934, the disclosures of which are herein incorporated by reference in their entirety.

In some embodiments, the stent 40 may include a covering, such as a bioabsorbable poly(lactic-co-glycolic acid (PLGA) membrane, on the abluminal (i.e., radially outward) and/or luminal (i.e., radially inward) surface of the stent 40. The covering may create a less traumatic interface between the vessel tissue and the stent 40 and/or enhance native tissue regrowth around the stent 40. In some instances, the covering may absorb at a different rate (e.g., faster or slower) than the material forming the stent structure itself. Additionally or alternatively, the covering on the abluminal surface may create a smooth lumen for advancing additional medical devices and medical device structures through the stent 40 once implanted.

In some instances, the stent covering may include a lubricant and/or biological coating to promote tissue growth and/or may include a therapeutic agent for delivery to the target location and subsequent eluding from the coating.

The terms "therapeutic agents," "drugs," "bioactive agents," "pharmaceuticals," "pharmaceutically active agents", and other related terms may be used interchangeably herein and include genetic therapeutic agents, non-genetic therapeutic agents, and cells. Therapeutic agents may be used singly or in combination. A wide range of therapeutic agent loadings can be used in conjunction with the devices of the present invention, with the pharmaceutically effective amount being readily determined by those of ordinary skill in the art and ultimately depending, for example, upon the condition to be treated, the nature of the therapeutic agent itself, the tissue into which the dosage form is introduced, and so forth.

Some specific beneficial agents include anti-thrombotic agents, anti-proliferative agents, anti-inflammatory agents, anti-migratory agents, agents affecting extracellular matrix production and organization, antineoplastic agents, anti-mitotic agents, anesthetic agents, anti-coagulants, vascular cell growth promoters, vascular cell growth inhibitors, cholesterol-lowering agents, vasodilating agents, and agents that interfere with endogenous vasoactive mechanisms.

More specific agents include paclitaxel, sirolimus, everolimus, tacrolimus, Epo D, dexamethasone, estradiol, halofuginone, cilostazole, geldanamycin, ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, and Serca 2 gene/protein, resiquimod, imiquimod (as well as other imidazoquinoline immune response modifiers), human apolioproteins (e.g., AI, AII, AIII, AIV, AV, etc.), vascular endothelial growth factors (e.g., VEGF-2), as well a derivatives of the forgoing, among many others.

Numerous additional therapeutic agents useful for the practice of the present invention may be selected from those described in paragraphs [0040] to [0046] of commonly assigned U.S. Patent Application Pub. No. 2003/0236514, the entire disclosure of which is hereby incorporated by reference.

The stent 40 may include radiopaque elements or include a radiopaque material to permit visualization of placement of the stent 40 with a fluoroscopy device, or other imaging technique. For example, the polymeric material forming the stent 40 may include iodine, or a metallic powder, such as tungsten or barium may be dispersed in the polymeric material forming the stent 40 to provide the stent 40 with a desired degree of radiopacity.

The stent 40 may be positioned on the balloon structure 20 such that the stent 40 surrounds a body portion 52 of the inflatable balloon structure 20, with a distal anchoring portion 60 of the inflatable balloon structure 20 positioned distal of the stent 40 and a proximal anchoring portion 62 of the inflatable balloon structure 20 positioned proximal of the stent 40. In some instances, the distal anchoring portion 60 of the inflatable balloon structure 20 may be configured to expand within a portion of the true lumen of the blood vessel distal of the occlusion and/or the proximal anchoring portion 62 of the inflatable balloon structure 20 may be configured to expand within a portion of the true lumen of the blood vessel proximal of the occlusion to anchor the recanalization catheter 10 from unintentional movement during expansion of the stent 40 in a subintimal pathway.

As shown in FIG. 1, in some instances, the body portion 52 may be a dilatation balloon 50, while the distal anchoring portion 60 may be a distal cone portion 54 of the dilatation balloon 50 extending between the body portion 52 and a distal waist of the dilatation balloon 50, and/or the proximal anchoring portion 62 may be a proximal cone portion 56 of the dilatation balloon 50 extending between the body portion 52 and a proximal waist of the dilatation balloon 50.

The distal anchoring portion 60 and/or the proximal anchoring portion 62 may be sufficiently sized and configured to anchor the recanalization catheter 10 in the vasculature to prevent unintentional displacement of the stent 40 in a subintimal pathway during deployment (e.g., expansion) of the stent 40 in the subintimal pathway.

For example, in an inflated configuration in which the body portion 52 is inflated to expand the stent 40 into an expanded configuration, as shown in FIG. 1, the distal anchoring portion 60 of the inflatable balloon structure 20 may have an outer diameter in the inflated configuration greater than an outer diameter of the stent 40 in the expanded configuration. Thus, as the stent 40 is expanded against vessel wall tissue defining the subintimal pathway, the diameter of the distal anchoring portion 60 may be sufficiently larger than the expanded diameter of the stent 40 to prevent displacement of the distal anchoring portion 60 proximally into the subintimal pathway from the true lumen distal of the occlusion.

Similarly, in an inflated configuration in which the body portion 52 is inflated to expand the stent 40 into an expanded configuration, as shown in FIG. 1, the proximal anchoring portion 62 of the inflatable balloon structure 20 may have an outer diameter in the inflated configuration greater than an outer diameter of the stent 40 in the expanded configuration. Thus, as the stent 40 is expanded against vessel wall tissue defining the subintimal pathway, the diameter of the proximal anchoring portion 62 may be sufficiently larger than the expanded diameter of the stent 40 to prevent displacement of the proximal anchoring portion 62 distally into the subintimal pathway from the true lumen proximal of the occlusion.

Furthermore, the length of the distal cone portion 54, forming the distal anchoring portion 60, may extend distal of the stent 40 for a distance of at least 10% of the length or at least 20% of the length of the stent 40 measured from a proximal end of the stent 40 to a distal end of the stent 40. The proximal cone portion 56 may extend proximally from the stent 40 in a similar fashion. For instance, the length of the proximal cone portion 56, forming the proximal anchoring portion 62, may extend proximal of the stent 40 for a distance of at least 10% of the length or at least 20% of the length of the stent 40 measured from a proximal end of the stent 40 to a distal end of the stent 40. Accordingly, for a stent 40 having a length of about 20 millimeters, the distal cone portion 54 and/or the proximal cone portion 56 may extend about 2 to about 4 millimeters beyond the ends of the stent 40, in some instances.

The inflatable balloon structure 20 may be configured such that the distal cone portion 54, forming the distal anchoring portion 60, and/or the proximal cone portion 56, forming the proximal anchoring portion 62, may be at least partially inflated prior to inflating the body portion 52 sufficiently to radially expand the stent 40 into the expanded configuration. For example, the distal cone portion 54 and/or the proximal cone portion 56 may be configured to be expanded at a lower pressure than the body portion 52, such that as the pressure within the inflatable balloon structure 20 is increased, the distal cone portion 54 and/or the proximal cone portion 56 are initially inflated to anchor the inflatable balloon structure 20, and thus the catheter 10, through the subintimal pathway prior to radially expanding the stent 40 in the subintimal pathway.

Figure 2:
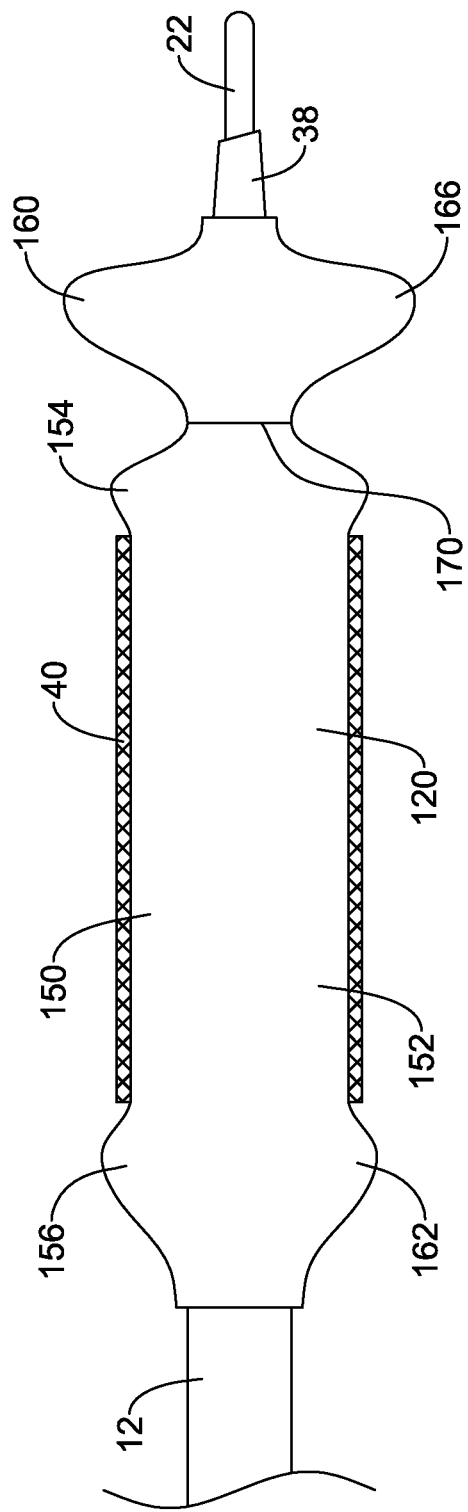
FIG. 2 is a side plan view of an alternative configuration of the distal portion of the catheter apparatus of FIG. 1.

FIG. 2 illustrates an alternative configuration of the distal portion of the recanalization catheter 10. As shown in FIG. 2, the recanalization catheter 10 includes an inflatable balloon structure 120 mounted on the distal portion of the catheter shaft 12.

The stent 40 may be positioned on the balloon structure 120 such that the stent 40 surrounds a body portion 152 of the inflatable balloon structure 120, with a distal anchoring portion 160 of the inflatable balloon structure 120 positioned distal of the stent 40 and a proximal anchoring portion 162 of the inflatable balloon structure 120 positioned proximal of the stent 40. In some instances, the distal anchoring portion 160 of the inflatable balloon structure 120 may be configured to expand within a portion of the true lumen of the blood vessel distal of the occlusion and/or the proximal anchoring portion 162 of the inflatable balloon structure 120 may be configured to expand within a portion of the true lumen of the blood vessel proximal of the occlusion to anchor the recanalization catheter 10 from unintentional movement during expansion of the stent 40 in a subintimal pathway.

As shown in FIG. 2, the body portion 152 may be a dilatation balloon 150, while the distal anchoring portion 160 may be a separate anchoring balloon 166 located on the catheter shaft 12 distal of the dilatation balloon 150. In such an embodiment, the dilatation balloon 150 may be in fluid communication with a first inflation lumen extending through the catheter shaft 12 and the anchoring balloon 166 may be in fluid communication with a second inflation lumen extending through the catheter shaft 12, thus permitting the anchoring balloon 166 to be inflated independent of the dilatation balloon 150. In other instances, the dilatation balloon 150 and the anchoring balloon 166 may both be in fluid communication with a single inflation lumen, with the anchoring balloon 166 configured to be at least partially inflated prior to inflating the dilatation balloon 150. For example, the anchoring balloon 166 may be configured to be inflated at a lower inflation pressure than the dilatation balloon 150.

Similar to the balloon structure 20, the proximal anchoring portion 162 may be a proximal cone portion 156 of the dilatation balloon 150 extending between the body portion 152 and a proximal waist of the dilatation balloon 150. The dilatation balloon 150 may also include a distal cone portion 154 located distal of the stent 40 which may aid in anchoring the recanalization catheter 10.

The distal anchoring portion 160 and/or the proximal anchoring portion 162 may be sufficiently sized and configured to anchor the recanalization catheter 10 in the vasculature to prevent unintentional displacement of the stent 40 in a subintimal pathway during deployment (e.g., expansion) of the stent 40 in the subintimal pathway.

The anchoring balloon 166 may be a separate member from the dilatation balloon 150, or the anchoring balloon 166 may be a distal extension of the dilatation balloon 150, with an intermediate waist 170 of the balloon structure 120 secured to the catheter shaft 12 between the dilatation balloon 150 and the anchoring balloon 166.

Figure 3:
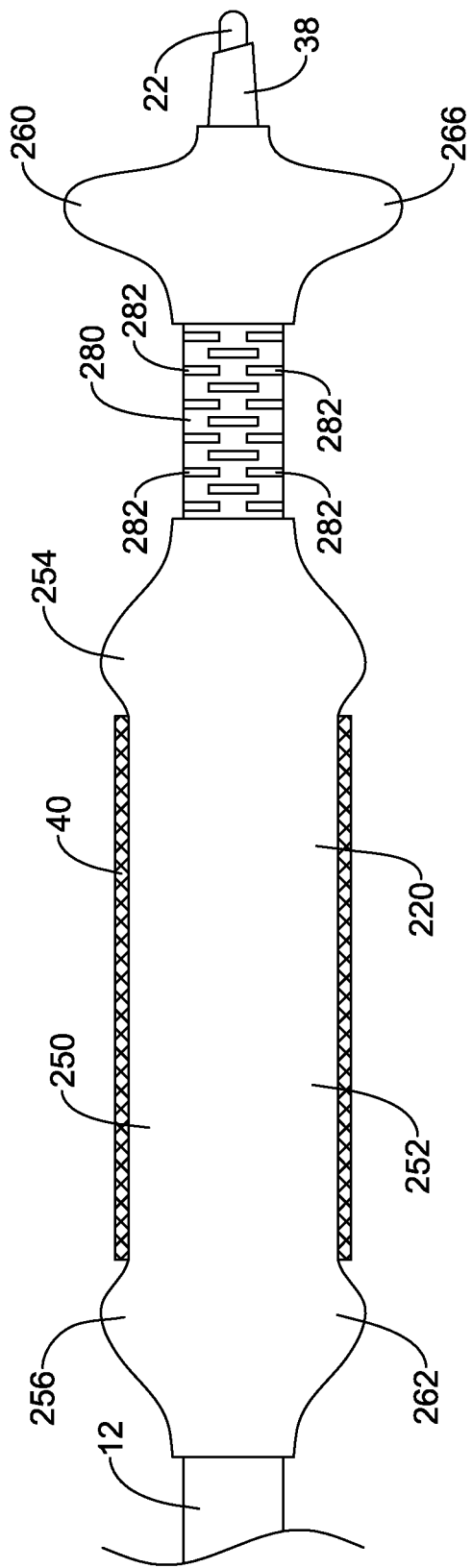
FIG. 3 is a side plan view of another alternative configuration of the distal portion of the catheter apparatus of FIG. 1.

FIG. 3 illustrates another alternative configuration of the distal portion of the recanalization catheter 10. As shown in FIG. 3, the recanalization catheter 10 includes an inflatable balloon structure 220 mounted on the distal portion of the catheter shaft 12.

The stent 40 may be positioned on the balloon structure 220 such that the stent 40 surrounds a body portion 252 of the inflatable balloon structure 220, with a distal anchoring portion 260 of the inflatable balloon structure 220 positioned distal of the stent 40 and a proximal anchoring portion 262 of the inflatable balloon structure 220 positioned proximal of the stent 40. In some instances, the distal anchoring portion 260 of the inflatable balloon structure 220 may be configured to expand within a portion of the true lumen of the blood vessel distal of the occlusion and/or the proximal anchoring portion 262 of the inflatable balloon structure 220 may be configured to expand within a portion of the true lumen of the blood vessel proximal of the occlusion to anchor the recanalization catheter 10 from unintentional movement during expansion of the stent 40 in a subintimal pathway.

As shown in FIG. 3, the body portion 252 may be a dilatation balloon 250, while the distal anchoring portion 260 may be a separate anchoring balloon 266 located on the catheter shaft 12 distal of the dilatation balloon 250. In such an embodiment, the dilatation balloon 250 may be in fluid communication with a first inflation lumen extending through the catheter shaft 12 and the anchoring balloon 266 may be in fluid communication with a second inflation lumen extending through the catheter shaft 12, thus permitting the anchoring balloon 266 to be inflated independent of the dilatation balloon 250. In other instances, the dilatation balloon 250 and the anchoring balloon 266 may both be in fluid communication with a single inflation lumen, with the anchoring balloon 266 configured to be at least partially inflated prior to inflating the dilatation balloon 250. For example, the anchoring balloon 266 may be configured to be inflated at a lower inflation pressure than the dilatation balloon 250.

Similar to the balloon structure 20, the proximal anchoring portion 262 may be a proximal cone portion 256 of the dilatation balloon 250 extending between the body portion 252 and a proximal waist of the dilatation balloon 250. The dilatation balloon 250 may also include a distal cone portion 254 located distal of the stent 40 which may aid in anchoring the recanalization catheter 10.

The distal anchoring portion 260 and/or the proximal anchoring portion 262 may be sufficiently sized and configured to anchor the recanalization catheter 10 in the vasculature to prevent unintentional displacement of the stent 40 in a subintimal pathway during deployment (e.g., expansion) of the stent 40 in the subintimal pathway.

The anchoring balloon 266 may be a separate member from the dilatation balloon 250, and a flexible member, such as a metallic hypotube 280 having a plurality of slots or slits 282 formed therein to provide a desired amount of lateral flexibility to the hypotube 280 may extend between the dilatation balloon 250 and the anchoring balloon 266. A distal waist of the dilatation balloon 250 may be secured to the hypotube 280 and a proximal waist of the anchoring balloon 266 may be secured to the hypotube 280. The hypotube 280, or other flexible member, extending between the dilatation balloon 250 and the anchoring balloon 266 may provide sufficient flexibility to the catheter shaft 12 to enable the dilatation balloon 250 to be positioned and inflated in the subintimal pathway while the anchoring balloon 266 is positioned and inflated in the true lumen of the blood vessel distal of the occlusion.

In some instances, it may be undesired, difficult or impossible to pass through an occlusion, such as a chronic total occlusion (CTO) in a lumen of a blood vessel with a medical device to recanalize the vessel. In such instances, it may be possible to recanalize the blood vessel through a subintimal approach using the recanalization catheter 10. Accordingly, FIGS. 4-8 illustrate aspects of an exemplary method for recanalizing a blood vessel 80 occluded by an occlusion 90 using the recanalization catheter 10.

The blood vessel 80 typically has three tissue layers, an innermost layer or intima layer (i.e., tunica intima) 82, an intermediate layer or media layer (i.e., tunica media) 84, and an outermost layer or adventitia layer (tunica adventitia) 86, with the media layer 84 positioned between the intima layer 82 and the adventitia layer 86. The intima layer 82 is a layer of endothelial cells lining the lumen 88 of the vessel 80, as well as a subendothelial layer made up of mostly loose connective tissue. The media layer 84 is a muscular layer formed primarily of circumferentially arranged smooth muscle cells. The adventitia layer 86, which forms the exterior layer of the vessel wall 80 is formed primarily of loose connective tissue made up of fibroblasts and associated collagen fibers.

Figure 4:
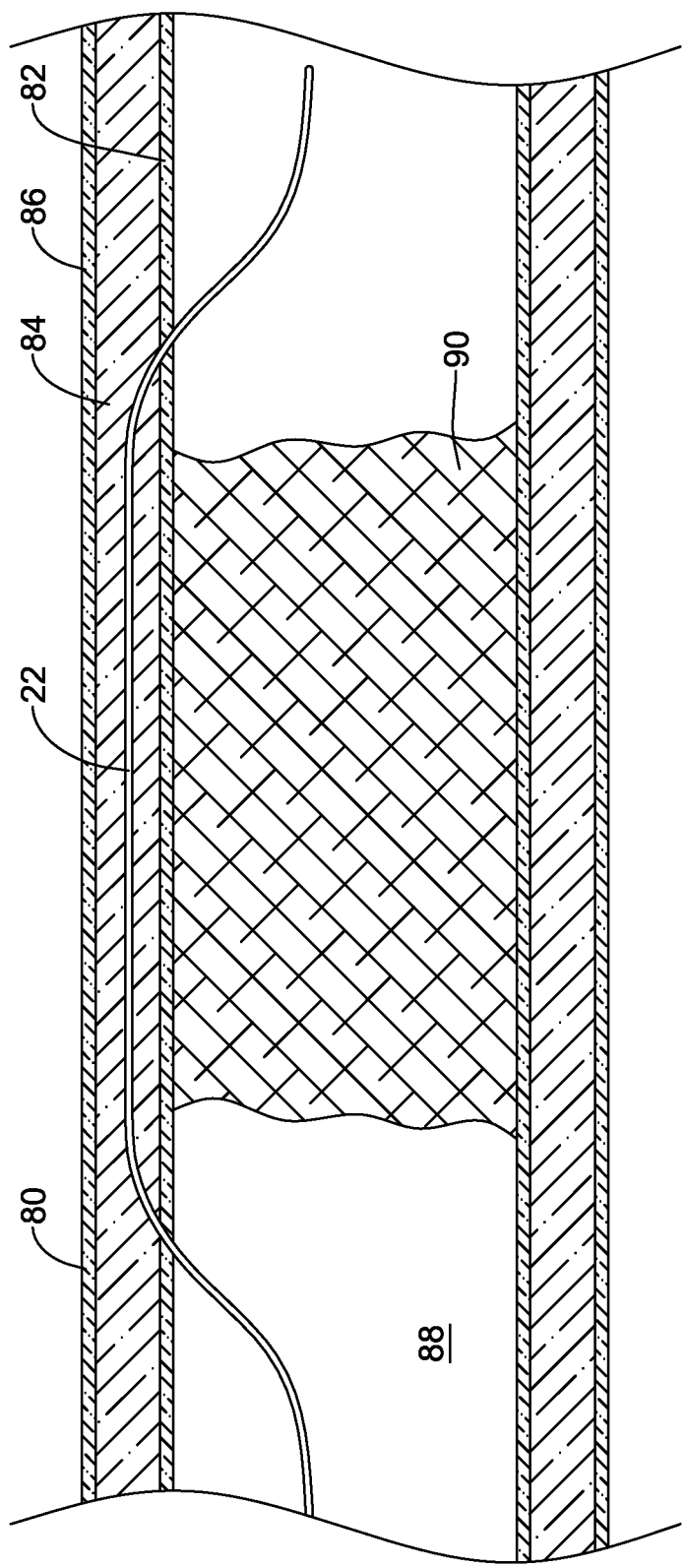
FIGS. 4-8 illustrate aspects of an exemplary method for recanalizing an occluded blood vessel using the catheter apparatus of FIG. 1.

As shown in FIG. 4, a subintimal pathway within the wall of the blood vessel 80 may initially be established to bypass the occlusion 90. As used herein, a subintimal pathway or space is a space between the intima layer 82 and the adventitia layer 86 created in the vessel wall 80, such as through dissection of the tissue layers of the vessel wall 80. For example, a guidewire 22 may initially be advanced through the lumen 88 of the vessel 80 to a location proximate a proximal end of an occlusion 90 blocking the lumen 88. The guidewire 22 may then be advanced to penetrate outward through the intima layer 82 at a location proximal of the proximal end of the occlusion 90 into the vessel wall 80. With the tip of the guidewire 22 located between the intima layer 82 and the adventitia layer 86, the guidewire 22 may be further advanced distally in a subintimal manner to create a subintimal space between the intima layer 82 and the adventitia layer 86. The guidewire 22 may be advanced in a subintimal manner until the distal tip of the guidewire 22 is located distal of the distal end of the occlusion 90 in the subintimal space created, such as by dissection of the tissue layers of the vessel wall 80. Once past the occlusion 90, the guidewire 22 may be directed back into the true lumen of the blood vessel 80 distal of the occlusion 90. Accordingly, the guidewire 22 may establish a subintimal track around the occlusion 90 from the true lumen proximal of the occlusion 90 to the true lumen distal of the occlusion 90 over which an additional medical device may be advanced to perform a medical procedure within the vasculature.

It is recognized that other techniques may be implemented in order to subintimally bypass an occlusion 90 with a guidewire or otherwise establish a subintimal track around the occlusion 90. For example, a re-entry catheter or other tissue penetrating device may be utilized to assist re-entering the true lumen distal of the occlusion 90 if needed.

Figure 5:
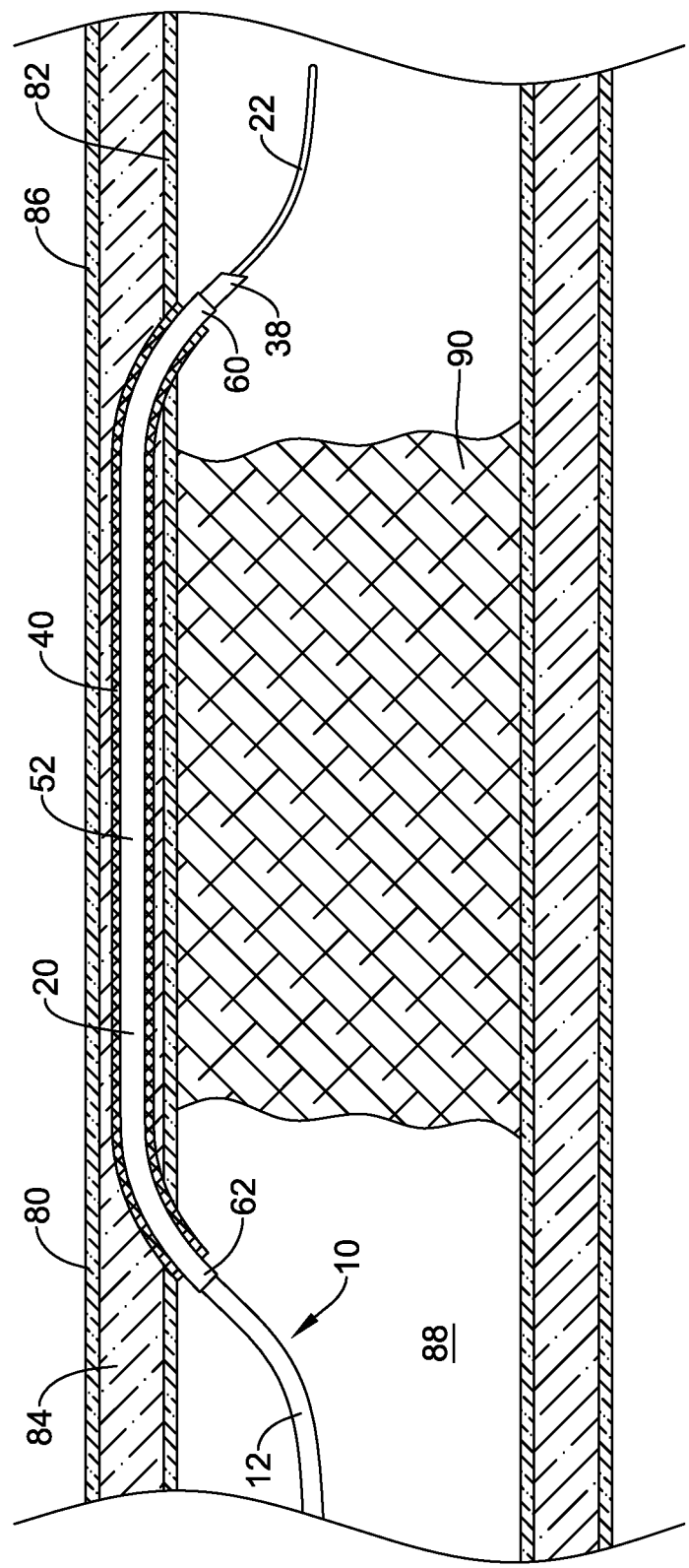

As shown in FIG. 5, the recanalization catheter 10 may then be advanced distally over the guidewire 22 from the true lumen 88 proximal of the occlusion 90, into the subintimal space between the intima layer 82 and the adventitia layer 86. The distal end of the recanalization catheter 10 may re-enter the true lumen distal of the occlusion 90, such that the body portion 52 of the balloon structure 20, with the stent 40 positioned thereon, may be positioned across the occlusion in the subintimal path. The recanalization catheter 10 may be advanced through the subintimal space in a delivery configuration, such as with the balloon structure 20 in a deflated, folded configuration with the stent 40 surrounding the folded balloon structure 20.

The recanalization catheter 10 may be positioned, such that the distal end of the stent 40 opens out to and/or extends into a distal true lumen portion of the vessel 80 distal of the occlusion 90, while the proximal end of the stent 40 opens out to and/or extends into a proximal true lumen portion of the vessel 80 proximal of the occlusion 90. Accordingly, the distal anchoring portion 60 of the balloon structure 20 may be positioned distal of the stent 40 in the true lumen distal of the occlusion 90 while the proximal anchoring portion 62 of the balloon structure 20 may be positioned proximal of the stent 40 in the true lumen proximal of the occlusion 90.

Figure 6:
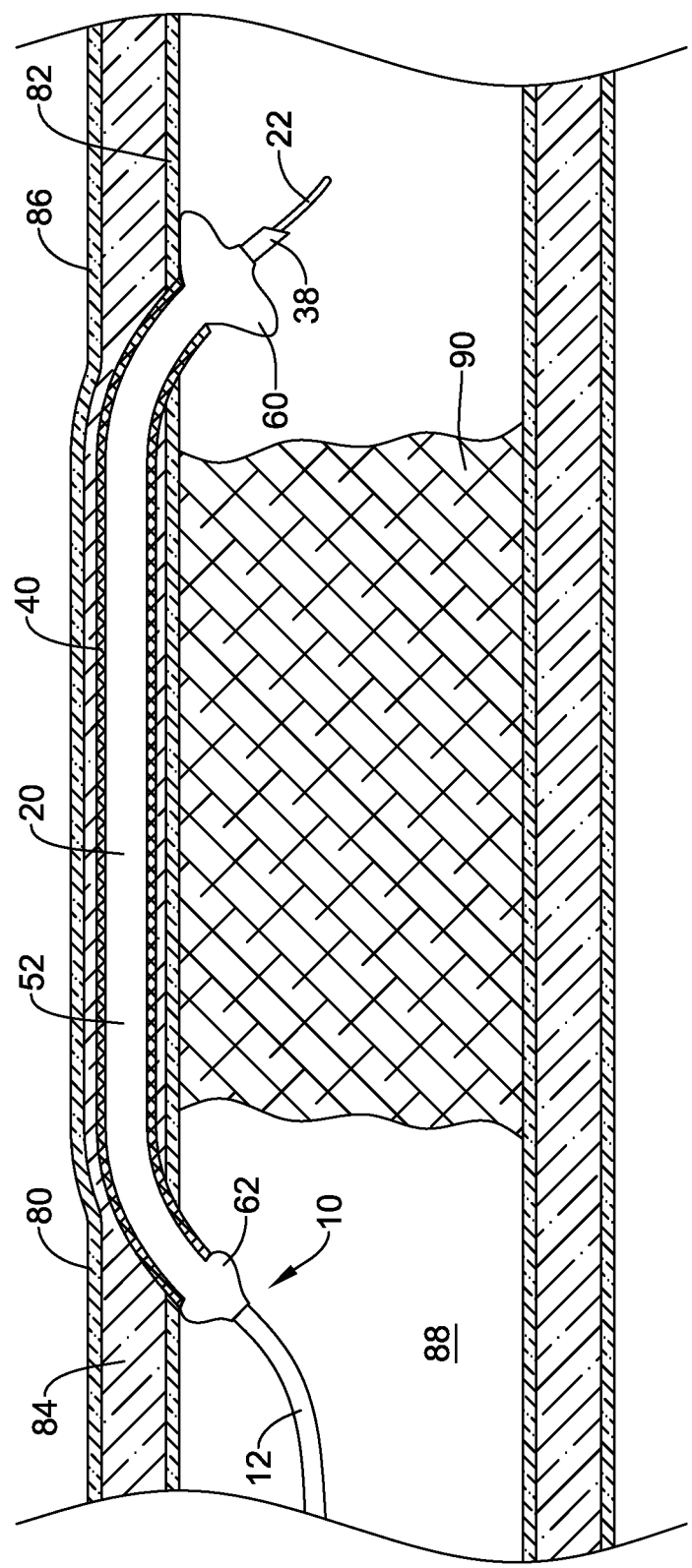

Once positioned through the subintimal pathway, the balloon structure 20 may be inflated with an inflation medium directed through an inflation lumen of the catheter shaft 12 to radially expand the stent 40 in the subintimal pathway, and thus maintain a pathway for subsequent blood flow around the occlusion 90. As shown in FIG. 6, the distal anchoring portion 60 may be inflated in the true lumen 88 distal of the occlusion 90 to anchor the inflatable balloon structure 20, including the body portion 52 underlying the stent 40, from unintentional proximal movement while the stent 40 is expanded in the subintimal pathway to maintain proper placement of the stent 40 in the subintimal pathway. Additionally or alternatively, the proximal anchoring portion 62 may be inflated in the true lumen 88 proximal of the occlusion 90 to anchor the inflatable balloon structure 20, including the body portion 52 underlying the stent 40, from unintentional distal movement while the stent 40 is expanded in the subintimal pathway to maintain proper placement of the stent 40 in the subintimal pathway. For instance, as can bee seen from FIG. 6, the distal anchoring portion 60 may be inflated against an intimal wall of the true lumen distal of the occlusion 90 and/or the proximal anchoring portion 62 may be inflated against an intimal wall of the true lumen proximal of the occlusion 90.

The distal anchoring portion 60 may be inflated to a diameter greater than the diameter of the distal opening of the subintimal pathway opening out to the true lumen distal of the occlusion 90 and/or the proximal anchoring portion 62 may be inflated to a diameter greater than the diameter of the proximal opening of the subintimal pathway opening out to the true lumen proximal of the occlusion 90. Thus, in the expanded state, the distal anchoring portion 60 may be prevented from being drawn into the subintimal space and/or the proximal anchoring portion 62 may be prevented from being drawn into the subintimal space, anchoring the balloon structure 20 in a desired position. Accordingly, the expandable stent 40 may have an expanded diameter in the subintimal pathway less than the diameter of the distal anchoring portion 60 and/or the proximal anchoring portion 62 of the inflatable balloon structure 20 in an inflated configuration.

In some instances, the distal anchoring portion 60 and/or the proximal anchoring portion 62 may be at least partially inflated prior to inflating the body portion 52 of the inflatable balloon structure 20. For example, the distal anchoring portion 60 and/or the proximal anchoring portion 62 may be inflated to a diameter greater than the diameter of the distal opening and the proximal opening, respectively, of the subintimal pathway prior to appreciable radial expansion of the stent 40 by the body portion 52 in the subintimal space.

In some embodiments, the distal anchoring portion 60 and/or the proximal anchoring portion 62 may be configured to be expanded at a lower pressure than the body portion 52, such that as the pressure within the inflatable balloon structure 20 is increased, the distal anchoring portion 60 and/or the proximal anchoring portion 62 are initially inflated to anchor the inflatable balloon structure 20, and thus the catheter 10, through the subintimal pathway prior to radially expanding the stent 40 in the subintimal pathway. Additionally or alternatively, the distal anchoring portion 60 and/or the proximal anchoring portion 62 may be molded or heat set to a desired shape, such that as the inflatable balloon structure 20 is pressurized, the distal anchoring portion 60 and/or the proximal anchoring portion 62 are inflated to a diameter sufficient to anchor the inflatable balloon structure 20, and thus the catheter 10, through the subintimal pathway prior to radially expanding the stent 40 in the subintimal pathway.

In other embodiments, the distal anchoring portion 60 and/or the proximal anchoring portion 62 may be inflated independent of inflating the body portion 52 of the inflatable balloon structure 20. For example, a separate inflation lumen may be in communication with each of the distal anchoring portion 60, the proximal anchoring portion 62 and/or the body portion 52 of the balloon structure 20. Thus, the distal anchoring portion 60 and/or the proximal anchoring portion 62 may be inflated prior to inflating the body portion 52 of the inflatable balloon structure 20.

Figure 7:
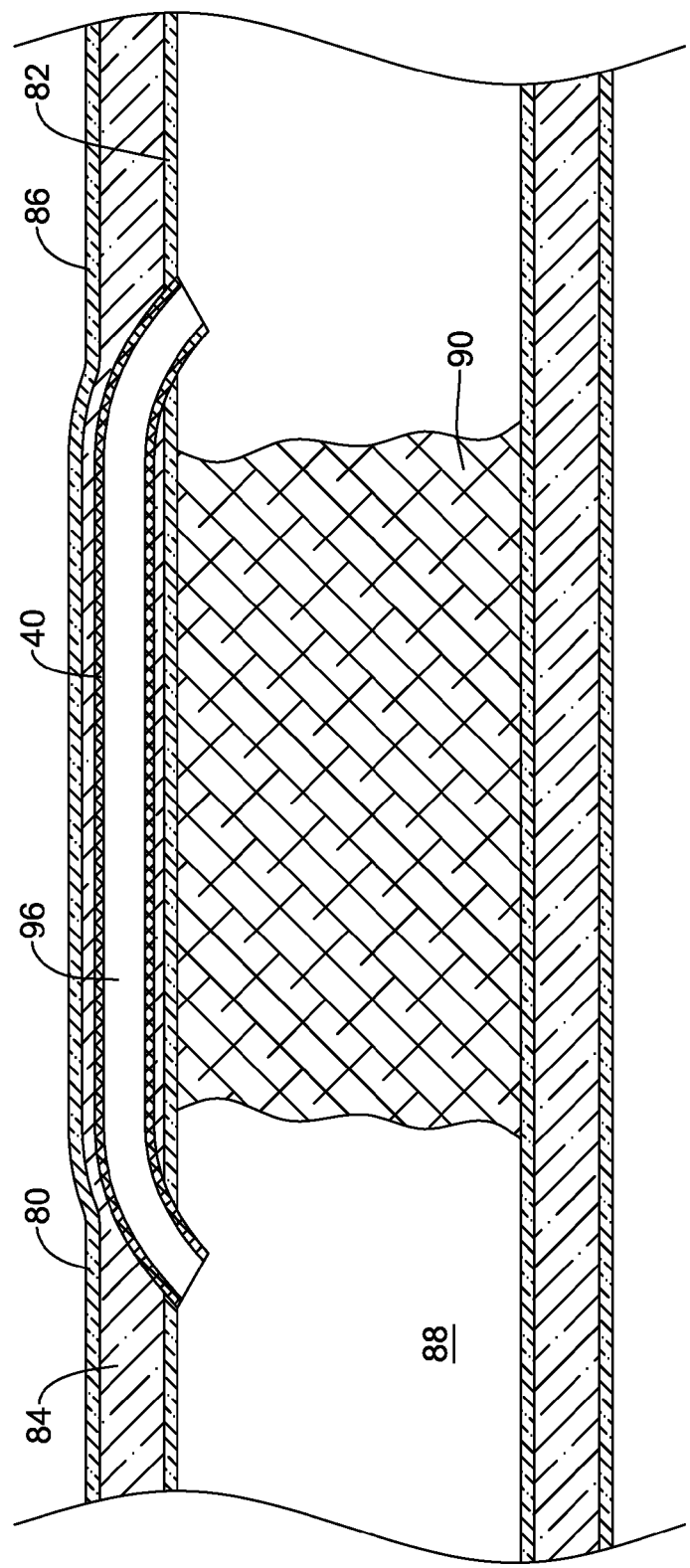

Once the stent 40 has been expanded, the balloon structure 20 may be deflated and the catheter 10 may be withdrawn proximally, leaving the stent 40 in the subintimal space in a radially expanded configuration. In some instances, the guidewire 22 may be retained through the subintimal space and in the true lumen distal of the occlusion 90 to guide additional medical devices to a further treatment site distal of the occlusion 90. Once the procedure is complete, the guidewire 22 may be withdrawn from the patient. FIG. 7 illustrates the radially expanded stent 40 forming a subintimal pathway 96 around the occlusion 90 immediately following a surgical procedure to implant the stent 40. The stent 40 may provide a scaffold structure supporting the subintimal pathway 96 to maintain patency for blood flow therethrough. The subintimal pathway 96 connects a true lumen portion of the vessel 80 proximal of the occlusion 90 to a true lumen portion of the vessel 80 distal of the occlusion 90 to create a by-pass for blood flow around the occlusion 90, and thus recanalize the vessel 80.

Figure 8:
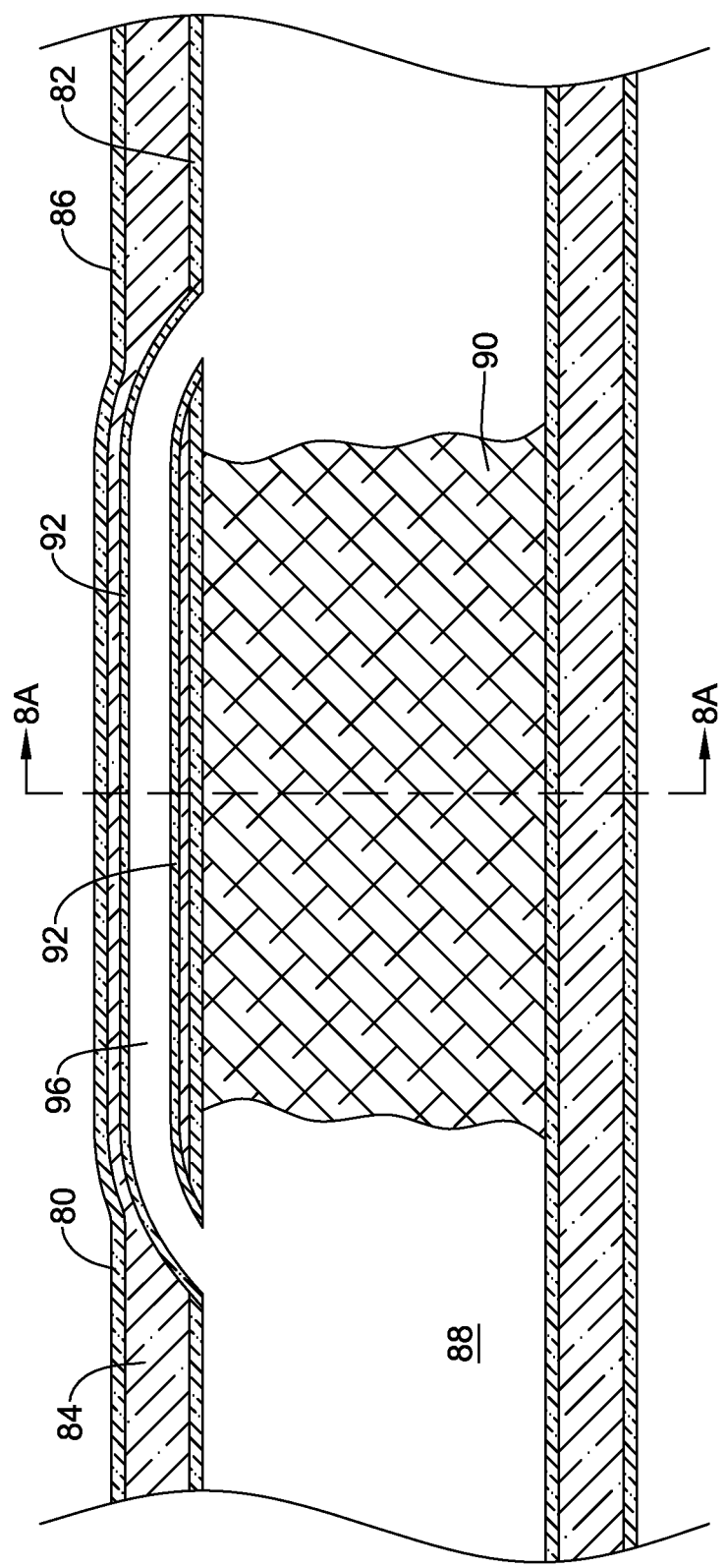
Figure 8A:
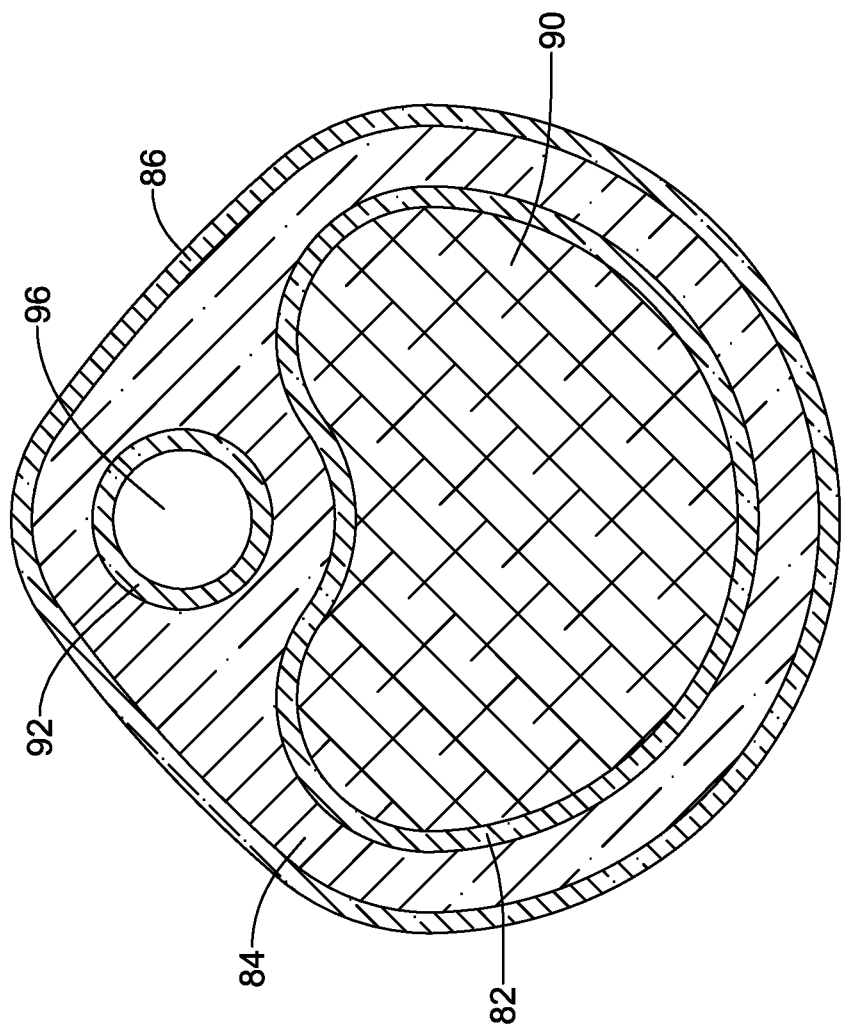
FIG. 8A is a cross-sectional view taken along line 8A-8A of FIG. 8 illustrating a pseudo-lumen including a superficial intima layer.

In some instances, the stent 40, which may be a bioabsorbable stent and/or include a biological coating to promote tissue growth, may be configured to promote native tissue regrowth around the stent 40 over a period of days, weeks or months to create a superficial intimal layer along the subintimal pathway 96. For instance, as shown in FIG. 8, over a period of time after the stent 40 has been implanted in the subintimal space, a superficial intimal layer 92 may develop to define the subintimal pathway 96. In other words, a circumferential superficial intimal layer 92 may be formed on the luminal surface of the subintimal pathway 96 from the proximal opening to the subintimal pathway 96 to the distal opening to the subintimal pathway 96. For example, as can be seen from the cross-sectional view of FIG. 8A, a circumferential superficial intimal layer 92 may be created between the intimal tissue layer 82 defining the true lumen 88 of the blood vessel 80 and the adventitial tissue layer 86 of the blood vessel 80. In some instances, the circumferential superficial intimal layer 92 may be created through the medial tissue layer 84 of the blood vessel 80. Thus, the superficial intimal layer 92 may be surrounded by tissue of the medial tissue layer 84, between the intimal tissue layer 82 defining the true lumen 88 of the blood vessel 80 and the adventitial tissue layer 86 of the blood vessel 80.

In some embodiments, the stent 40, or a portion thereof, may be bioabsorbable such that the stent 40 may be absorbed by the patient's body over a period of time, leaving the superficial intimal layer 92 forming the luminal surface of the subintimal pathway 96 around the occlusion 90. Thus, over a period of time, such as days, weeks or months, the stent 40 may be dissolved and leave behind a functioning vessel lumen around the occlusion 90 with native tissue creating a circumferential superficial intimal layer 92 adjacent to the occluded true lumen 88.

Those skilled in the art will recognize that aspects of the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A recanalization catheter assembly for establishing a subintimal pathway around an occlusion in a blood vessel, the recanalization catheter assembly comprising:
    an elongate catheter shaft extending distally from a hub assembly;
    an inflatable balloon structure mounted on a distal portion of the catheter shaft, the inflatable balloon structure configured to be expanded from a deflated configuration to an inflated configuration with a fluid delivered to an interior of the inflatable balloon structure through an inflation lumen extending through the catheter shaft;
    a stent surrounding a body portion of the inflatable balloon structure;
    wherein the inflatable balloon structure includes a proximal anchoring portion positioned proximal of the stent and a distal anchoring portion positioned distal of the stent;
    wherein the proximal anchoring portion of the inflatable balloon structure is configured to expand within a true lumen portion of the blood vessel proximal of the occlusion to anchor the recanalization catheter from unintentional movement during expansion of the stent in the subintimal pathway;
    wherein the distal anchoring portion of the inflatable balloon structure is configured to expand within a true lumen portion of the blood vessel distal of the occlusion to anchor the recanalization catheter from unintentional movement during expansion of the stent in the subintimal pathway;
    wherein the distal anchoring portion of the inflatable balloon structure has a radially outermost diameter in the inflated configuration greater than an outer diameter of the stent in a fully expanded configuration; and
    wherein the outermost diameter of the distal anchoring portion in the inflated configuration is greater than an outermost diameter of the proximal anchoring portion in the inflated configuration.

2. The recanalization catheter assembly of claim 1, wherein the stent has a length measured from a proximal end of the stent to a distal end of the stent, wherein the distal anchoring portion of the inflatable balloon structure extends distal of the stent for a distance of at least 10% of the length of the stent.

3. The recanalization catheter assembly of claim 1, wherein the stent has a length measured from a proximal end of the stent to a distal end of the stent, wherein the distal anchoring portion of the inflatable balloon structure extends distal of the stent for a distance of at least 20% of the length of the stent.

4. The recanalization catheter assembly of claim 1, wherein the distal anchoring portion of the inflatable balloon structure is inflatable independent of inflation of the body portion of the inflatable balloon structure.

5. The recanalization catheter assembly of claim 4, wherein the distal anchoring portion is an anchoring balloon and the body portion is a dilatation balloon distinct from the anchoring balloon.

6. The recanalization catheter assembly of claim 5, further comprising a slotted tubular member extending between the dilatation balloon and the anchoring balloon.

7. The recanalization catheter assembly of claim 1, wherein the body portion is a dilatation balloon and the distal anchoring portion is a distal cone portion of the dilatation balloon.

8. A recanalization catheter assembly for establishing a subintimal pathway around an occlusion in a blood vessel, the recanalization catheter assembly comprising:
- an elongate catheter shaft extending distally from a hub assembly;
- an inflatable balloon structure mounted on a distal portion of the catheter shaft, the inflatable balloon structure configured to be expanded from a deflated configuration to an inflated configuration with a fluid delivered to an interior of the inflatable balloon structure through an inflation lumen extending through the catheter shaft;
- a stent surrounding a body portion of the inflatable balloon structure;
- wherein the inflatable balloon structure includes a proximal anchoring portion positioned proximal of the stent and a distal anchoring portion positioned distal of the stent;
- wherein the proximal anchoring portion of the inflatable balloon structure is configured to expand within a true lumen portion of the blood vessel proximal of the occlusion to anchor the recanalization catheter from unintentional movement during expansion of the stent in the subintimal pathway;
- wherein the distal anchoring portion of the inflatable balloon structure is configured to expand within a true lumen portion of the blood vessel distal of the occlusion to anchor the recanalization catheter from unintentional movement during expansion of the stent in the subintimal pathway;
- wherein the proximal anchoring portion of the inflatable balloon structure has an outermost diameter in the inflated configuration greater than an outer diameter of a proximal end of the stent in an expanded configuration; and
- wherein an outermost diameter of the distal anchoring portion in the inflated configuration is greater than the outermost diameter of the proximal anchoring portion in the inflated configuration.

9. The recanalization catheter assembly of claim 8, wherein the stent has a length measured from a proximal end of the stent to the distal end of the stent, wherein the distal anchoring portion of the inflatable balloon structure extends distal of the stent for a distance of at least 10% of the length of the stent.

10. The recanalization catheter assembly of claim 8, wherein the stent has a length measured from the proximal end of the stent to a distal end of the stent, wherein the distal anchoring portion of the inflatable balloon structure extends distal of the stent for a distance of at least 20% of the length of the stent.

11. The recanalization catheter assembly of claim 8, wherein the body portion is a dilatation balloon and the distal anchoring portion is a distal cone portion of the dilatation balloon.

* * * * *